United States Patent [19]

Friauf et al.

[11] Patent Number: 5,298,742
[45] Date of Patent: Mar. 29, 1994

[54] LIGHT SENSOR FOR PHOTO-DYNAMIC THERAPY HAVING A TRANSPARENT HOUSING

[75] Inventors: Walter S. Friauf, Bethesda, Md.; Harvey I. Pass, McLean, Va.; Joseph F. Fessler, Walkersville, Md.

[73] Assignee: The United States of America as represented by Department of Health & Human Services, Washington, D.C.

[21] Appl. No.: 21,767

[22] Filed: Feb. 24, 1993

[51] Int. Cl.⁵ ................................................ H01J 5/02
[52] U.S. Cl. ..................... 250/239; 250/214.1; 257/433
[58] Field of Search ............... 250/239, 214.1, 214 R, 250/370.15, 235; 257/433, 434

[56] References Cited

U.S. PATENT DOCUMENTS

| | | |
|---|---|---|
| 2,689,313 | 9/1954 | Pakswer et al. . |
| 2,773,158 | 12/1956 | Myers . |
| 2,779,811 | 1/1957 | Picciano et al. . |
| 2,806,929 | 9/1957 | Langevin . |
| 3,092,997 | 6/1963 | Gaskill . |
| 3,753,197 | 8/1973 | Tachihara et al. . |
| 3,769,974 | 11/1973 | Smart et al. . |
| 3,818,451 | 6/1974 | Coleman . |
| 3,938,177 | 2/1976 | Hansen et al. . |
| 4,203,792 | 5/1980 | Thompson . |
| 4,307,934 | 12/1981 | Palmer . |
| 4,478,588 | 10/1984 | Lockard . |
| 5,041,727 | 8/1991 | Kojima et al. ................ 250/370.15 |
| 5,131,391 | 7/1992 | Sakai et al. . |
| 5,216,248 | 6/1993 | Ikeda et al. ..................... 250/214.1 |

Primary Examiner—David C. Nelms
Assistant Examiner—Que T. Le
Attorney, Agent, or Firm—Morgan & Finnegan

[57] ABSTRACT

A light sensor constructed from a commercial photodiode packaged in a transparent housing of sufficient thickness to set the photodetector away from the underlying surface, thereby reducing the shadowing effects of the photodetector and allowing incident light to pass through the housing to the tissue below. Electrical connections are made directly on the photodiode which is sealed within the transparent housing, thus avoiding electrical shock or short circuit hazards. The transparent package is equipped with four hooks which are well suited for attachment to tissue structure, either directly or with the aid of sutures. In a second embodiment, the light sensor includes a second photodiode mounted within the sealed housing to measure light reflected from the underlying tissue. The light sensor is well suited for use with photodynamic therapy.

8 Claims, 2 Drawing Sheets

LIGHT SENSOR FOR PHOTO-DYNAMIC THERAPY HAVING A TRANSPARENT HOUSING

BACKGROUND OF THE INVENTION

The present invention relates generally to light detection and packaging and, more particularly, to a device for sensing incident light during photodynamic therapy.

Photodynamic therapy (PDT) is an investigational therapy for myriad human cancers. PDT has been applied as a primary tumor treatment, as an adjunct to surgical tumor resection (i.e., intraoperative PDT), and has been extended as a large area treatment. Generally, PDT involves first treating the tissue with a photosensitizer, followed by illuminating the tissue, typically using a laser source. Evidently, in order to carefully investigate and use PDT, in-situ monitoring of the incident light intensity is required so that the intensity and total dose may be controlled. Not only is it important to measure the incident light intensity, but also it should be measured in real-time during PDT because variations in the laser output or changes in the transparency of the intravesical or intralipid fluid (e.g., due to bleeding) result in fluctuations in the light reaching the tissue surface. The light intensity impinging on surrounding regions due to scattering or reflection should also be measured to avoid potentially detrimental effects.

Presently, in-situ dosimetry devices have been developed which use an integrating sphere at the end of an optical fiber. This device is well-suited for bladder cases in which it is positioned via a catheter. However, since the integrating sphere has a large acceptance angle, it is sensitive to reflected light which renders accurate dosimetry more difficult. Also, the integrating sphere dosimetry device is not easily adaptable for use in other cancers. In applying PDT to other cancers, calculations based on laser power, target surface area, target shape, and reflectivity have been used to estimate the light intensity. Such calculations may be highly inaccurate due to factors such as non-ideal geometry, dynamic changes in the transmission and reflectivity of the intralipid and tissue, respectively, as well as changes in the laser output power. Thus, in order to better understand and control PDT, there is a clear need for further developments in sensors for use with PDT.

Accordingly, an object of the present invention is to provide a light sensor for use with PDT.

Another object of the present invention is to provide a light sensor structure which is safe for use on human patients, and particularly, a light sensor which prevents electrical hazards.

A related object of the present invention is that the light sensor measure light incident on the underlying tissue or surface while being insensitive to light reflected from the tissue.

A further object of the present invention is to provide a light sensor which does not prevent the underlying tissue or surface from being radiated by the incident light.

Another object of the present invention is that the light sensor includes a simple, effective means for attaching the sensor to the nearby tissue.

Yet a further object of the present invention is to provide a light sensor which is well-suited for attaching a plurality of these light sensors in the region undergoing PDT.

Yet another object of the present invention is to provide a sensor which separately and simultaneously measures the incident and reflected light.

The foregoing specific objects and advantages of the invention are illustrative of those which can be achieved by the present invention and are not intended to be exhaustive or limiting of the possible advantages which can be realized. Thus, these and other objects and advantages of the invention will be apparent from the description herein or can be learned from practicing the invention, both as embodied herein or as modified in view of any variations which may be apparent to those skilled in the art.

SUMMARY OF THE INVENTION

The above objects and advantages are achieved by a light sensor constructed from a commercial photodiode packaged in a transparent housing of sufficient thickness to set the photodetector away from the underlying tissue, thereby reducing the shadowing effects of the photodetector and allowing incident light to pass through the housing to the tissue below. Preferably, in order to further minimize shadowing, the photodetector itself has a small area relative to the average scattering length. Electrical connections are made directly on the photodiode which is sealed within the transparent housing, thus avoiding electrical shock or short circuit hazards. The transparent package is equipped with wire hooks which are well suited for attachment to tissue structure, either directly or with the aid of sutures.

In a further embodiment, a second photodiode is mounted within the sealed housing to measure light reflected from the underlying tissue. The second photodiode may be separately mounted or may be integrally formed on the backside of the first photodiode during photodiode microfabrication.

Used in conjunction with PDT, at least one of these sensors is mounted to the tissue which will be irradiated either directly or indirectly. The sensor structure enables underlying tissue to be irradiated while the photodetector is in place, prevents electrical hazards by eliminating external electrical connections near the housing, and provides a means for secure attachment to tissue. Although the present invention is intended for use with photodynamic therapy (PDT), such a sensor may find myriad application where the attendant advantages of the sensor are desired.

It will be appreciated by those skilled in the art that the foregoing brief description and the following detailed description are exemplary and explanatory of the present invention, but are not intended to be restrictive thereof or limiting of the advantages which can be achieved by the invention. Thus, the accompanying drawings, referred to herein and constituting a part hereof, illustrate preferred embodiments of the invention and, together with the detailed description, serve to explain the principles of the invention.

BRIEF DESCRIPTION OF THE DRAWINGS

The invention will be described in greater detail below by way of reference to the accompanying drawings, wherein.

DETAILED DESCRIPTION OF THE PREFERRED EMBODIMENT

Figure 1:
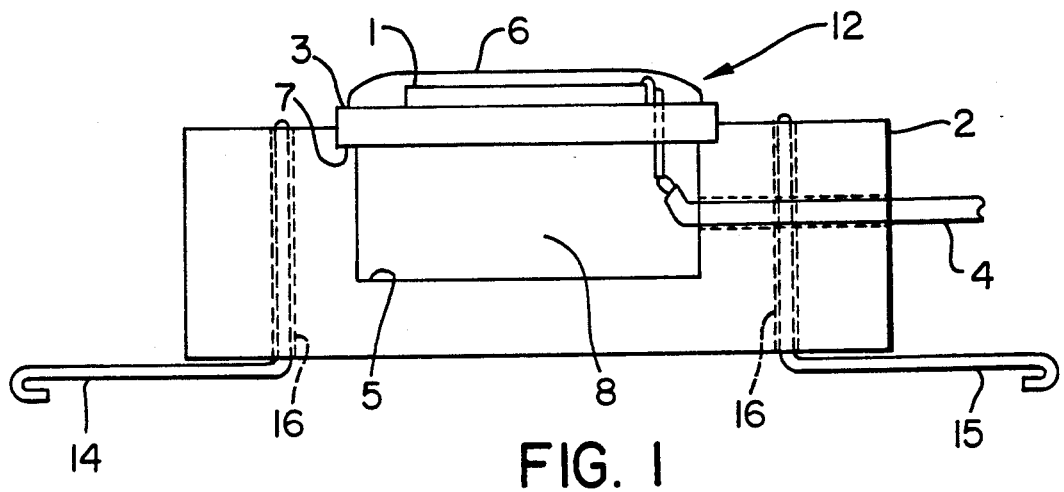
FIG. 1 is a cross-sectional view of a light sensor according to the present invention.
Figure 3:
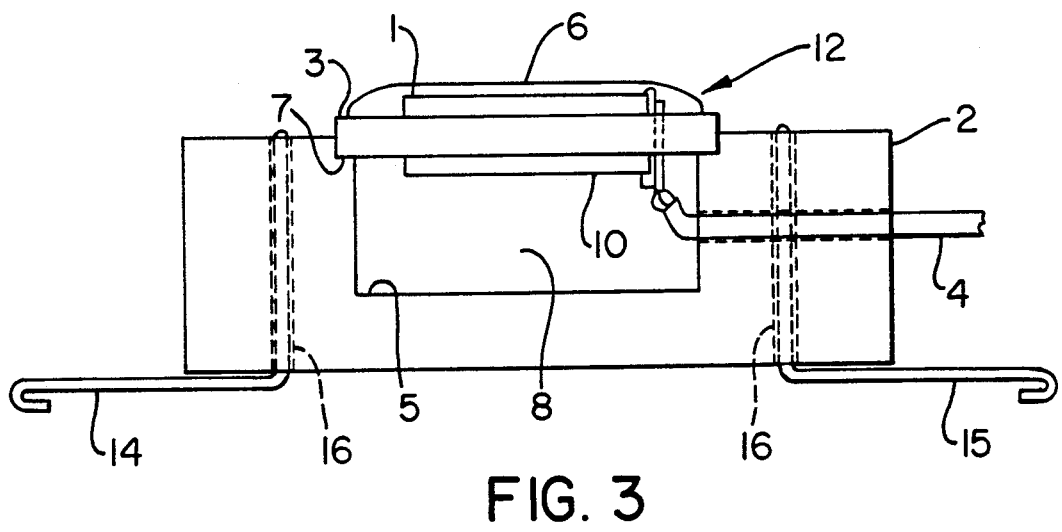
FIG. 3 is a cross-sectional view of the light sensor structure according to another embodiment of the present invention.
Figure 2:
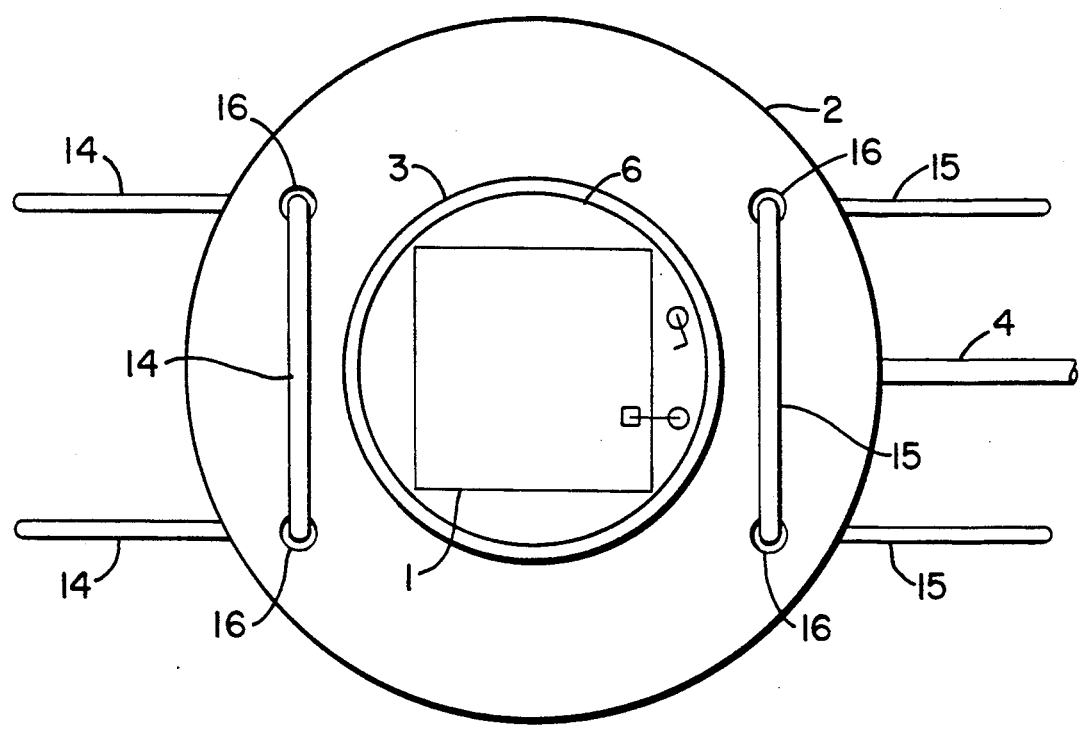
FIG. 2 is a top view of the light sensor according to the present invention.

Referring now to the accompanying drawings, wherein like reference characters refer to like parts throughout the various views, there are shown in FIGS. 1-3 the preferred embodiments of the light sensor according to the present invention.

FIG. 1 illustrates an embodiment of the present invention in which the light sensor structure includes a photo-sensitive member 12 mounted on a transparent base 2. An insulated cable 4, which is preferably coaxial to enhance shielding from interference, is inserted through a bore in the transparent base 2 and conductors within the insulated cable 4 are connected to the photosensitive member 12. An insulating transparent adhesive compound 8 bonds the photo-sensitive member 12 to the transparent base 2, and insulates the electrical connections.

The photo-sensitive member 12 may be a commercial packaged photodiode such as an EG&G Vactec model VTB 4051, which includes a photodiode 1 mounted on a package 3 and covered with an epoxy 6 which preferably has an index of refraction comparable to that of the adjacent medium during photodynamic therapy. The electrode contacts of the photodiode 1 are separately connected to electrode terminals of the package 3, which is typically opaque. Preferably, the photodiode 1 and package 3 have small, comparable diameters in order to minimize shadowing. The overall thickness of the photodiode 1 and package 3 should also be minimized to avoid shadowing. When a light diffusion aid is used in conjuction with large area PDT, the photodiode diameter should be negligible compared to the average scattering distance, which is on the order of one centimeter for 630 nm light in 0.02% intralipid.

Since electrical connections could be made directly from the insulated cable 4 to the photodiode contacts, the package 3 could be eliminated from the photosensitive member 12, thereby reducing shadowing. The package 3, however, provides a standard, convenient means for mounting, and making electrical connections to, the photodiode 1, and also provides mechanical support against photodiode fracture. Alternatively, the package 3 could be constructed from a transparent material, with metal used only for electrode terminals.

The transparent base 2 contains a recess 5, and has a bore extending radially from the outer wall to the inner wall formed by the recess 5. In order to facilitate attaching the photo-sensitive member 12, a second, shallower recess 7 which mates with the photosensitive member 12 is formed in the transparent base 2. The transparent base 2 may be constructed of lucite or other material which is transparent to the radiation that will be used during PDT. In order to provide strain relief for the insulated cable 4, the bore diameter is approximately equal to the diameter of the insulated cable 4, which is chosen small in order to minimize shadowing. The distance from the top surface of the transparent base to the opposite, bottom surface is designed to set the photo-sensitive member 12 away from the bottom surface to reduce the shadowing effect of the photodiode 1.

During fabrication of the sensor, the insulated cable 4 is coaxially fitted into the bore, and the ends of the conductive wires contained within the insulated cable 4 are then connected (e.g., soldered) to the package 3 electrode terminals which correspond to the photodiode electrode contacts. The recess 5 is then filled with an electrically insulating transparent adhesive compound 8 followed by press fitting the photosensitive member 12 onto the top surface of the transparent base 2, within the recess 7.

The electrically insulating transparent adhesive compound 8, which is preferably medical grade silastic compound, may require curing by heat treatment. In addition to affixing the photo-sensitive member 12, the insulating transparent adhesive compound 8 seals the recess 5 and bore, thus isolating the electrical connections within the transparent base 2, as well as affixing the insulated cable 4 to the transparent housing which assists the strain relief of the cable 4.

Referring to FIG. 1 and FIG. 2, a tissue attachment means is also provided. Each of a pair of wires 14 and 15 is threaded through a separate pair of bores 16 which extend from the front to the back of the lucite base. The two ends of each wire emanate from the package's bottom and are shaped into the plane of the bottom surface of the transparent base 2, and the ends are formed into hooks adapted for attachment to tissue. In FIG. 2 the pair of wires 14 and 15 are parallel to facilitate attachment between ribs when used in the chest cavity. Suturing may also be required; however, the hooks assist the initial placement of the sensor and the suturing procedure. In order to assist securing the photosensitive member 12 to the transparent base 2, the bores 16 and wires 14 and 15 may be arranged so that the wires overlap the edges of the package 3 or photodiode 1. Furthermore, the tissue attachment means may be adapted as required for attachment to different tissue structures. For instance, a lucite annulus having holes for suturing may be preferable to the hooks when used on the pericardium.

FIG. 3 depicts another embodiment of the present invention. As described hereinabove, the tissue reflects a fraction of the incident light. Furthermore, the amount of reflection may be time dependent because of changes in the tissue surface structure during PDT. Thus, measuring the incident light intensity may not be an accurate measure of the light intensity which is transmitted to the tissue. The sensor shown in FIG. 3 assists in determining the transmitted light flux by measuring both the incident and reflected light to and from the tissue, respectively. The reflected light is measured by a second photodiode 10 mounted on the opposite side of the package 3, which is adapted to include separate electrode terminals for the second photodiode 10. Indeed, it would be expedient to mount two separate commercial packaged photodiodes back-to-back; however, the overall thickness of this structure may result in substantial shadowing, and therefore, the embodiment shown in FIG. 3 depicts two photodiodes 1 and 10 mounted on opposite faces of a single package 3.

Overall construction of the sensor remains unchanged, except that cable 4 includes a separate pair of wires for connection to the electrode terminals corresponding to photodiode 10. Note, however, that adding photodiode 10 may require only one additional electrode terminal on package 3 and one additional wire in cable 4, since the photodiodes 1 and 10 may be connected with one electrode contact in common.

Also, it may be possible to form oppositely facing photodiodes on a single substrate, thereby eliminating the need to mount two separate photodiodes to package 3. In this case, package 3 could be adapted to have a hole which is overlapped by the mounted photodiode substrate, thus exposing the active area of the photodiode facing the package 3. Alternatively, package 3 could be eliminated and the photodiode mounted directly to the transparent base 2. As discussed above, however, package 3 is a convenient, standard means for mounting, and making electrical connections to, the photodiode, and also provides mechanical support against fracture of the photodiode.

Prior to using these sensor structures, careful calibration should be performed. For instance, light transmission through the transparent base 2 should be measured, as well as the amount of actual shadowing by the photodiode 1, package 3, and cable 4. During PDT, one or more of either type of sensor is attached in the region of interest, and the opposite end of cable 4 is connected to an appropriate signal receiving means. Preferably, the photodiodes are zero-biased to avoid possible shock hazards, and the signal receiving means includes a preamplifier stage followed by analog-to-digital conversion. The digital signals can then be used by any suitable digital processor, such as a personal computer. Isolation of high voltage signals from the sensor structures can be achieved by using isolation transformers and/or opto-isolators.

Although the above description provides many specificities, these enabling details should not be construed as limiting the scope of the invention, and it will be readily understood by those persons skilled in the art that the present invention is susceptible to many modifications, adaptations, and equivalent implementations without departing from this scope. For example, the photodiode 1 may be replaced by any suitable photodetector. Also, the recess 5 may instead be formed in the back surface of the transparent housing; however, sealing the recess would require ensuring a planar back surface, which is required to facilitate mounting the sensor flushly against the underlying tissue. Additionally, a light sensor structure having similar structure and attendant advantages may be manufactured using standard plastic molding technology by connecting the photo-sensitive member to the insulated cable followed by the molding process which forms the transparent base to enclose the photo-sensitive member and connected cable. This molding method eliminates the requirement of machining the transparent base, using an insulating adhesive compound, and inserting the insulated cable through the bore prior to connecting the wires to the photo-sensitive member. The hereinabove preferred embodiment, however, is advantageous for easily and inexpensively manufacturing the light sensor with simple facilities, and for adapting the light sensor design for specific applications.

These and other changes can be made without departing from the spirit and the scope of the invention and without diminishing its attendant advantages. It is therefore intended that the present invention is not limited to the disclosed embodiments but should be defined in accordance with the claims which follow.

We claim:

1. A photo-sensitive sensor comprising:
   a transparent base having a top surface, a bottom surface, and an outer wall surface, said top surface having a recess thereby forming an inner wall surface, said transparent base having a bore extending from said outer surface to said inner surface;
   a first photo-sensitive member having a light-sensitive region for generating an electrical signal corresponding to the intensity of light incident thereto, and conductive electrodes connected to said light-sensitive region, said first photo-sensitive member mounted on said top surface and disposed over said recess;
   an insulated cable coaxially inserted in said bore, having conductive wires connected to said conductive electrodes;
   an electrically insulating transparent adhesive compound filling said recess, thereby bonding said photoconductive member to said transparent base and sealing said conductive electrodes and said conductive wires.

2. The photo-sensitive sensor of claim 1, wherein said photo-sensitive member includes a photodiode mounted on a package having conductive electrode terminals, said photodiode having conductive electrode contacts connected to said conductive electrode terminals.

3. The photo-sensitive sensor of claim 1, wherein said transparent base has four attachment bores extending from said top surface to said bottom surface, and further comprising a pair of wire members, each wire member extending through a separate pair of said attachment bores, each end of each wire member formed into a hook, thereby providing an attachment means.

4. The photo-sensitive sensor of claim 1, further comprising a second photo-sensitive member having a light-sensitive region for generating an electrical signal corresponding to the intensity of light incident thereto, and conductive electrodes connected to said light-sensitive region, said second photo-sensitive member mounted adjacent to said first photo-sensitive member with respective said light sensitive-region of said first and second photo-sensitive members oppositely disposed, and wherein said insulated cable includes at least one additional wire for connecting to at least one of said conductive electrodes of said second photo-sensitive member.

5. The photo-sensitive sensor of claim 1, wherein said electrically insulating transparent adhesive compound is silastic compound.

6. The photo-sensitive sensor of claim 1, wherein said transparent base is formed from lucite.

7. A photo-sensitive sensor comprising:
   a first photo-sensitive member having a light-sensitive region for generating an electrical signal corresponding to the intensity of light incident thereto, and conductive electrodes connected to said light-sensitive region;
   an insulated cable having conductive wires connected to said conductive electrodes;
   an insulating transparent base having a top surface, a bottom surface, and an outer wall surface, said insulating transparent base enclosing said first photo-sensor member and portion of said insulated cable which extends into said insulating transparent base through said outer wall surface, thereby electrically insulating said conductive wires and said conductive electrodes, said photo-sensitive member adjacently disposed to said top surfaces.

8. The photo-sensitive sensor of claim 7, further comprising a second photo-sensitive member having a light-sensitive region for generating an electrical signal corresponding to the intensity of light incident thereto, and conductive electrodes connected to said light-sensitive region, said second photo-sensitive member mounted adjacent to said first photo-sensitive member with respective said light sensitive-region of said first and second photo-sensitive members oppositely disposed, and wherein said insulated cable includes at least one additional wire for connecting to at least one of said conductive electrodes of said second photo-sensitive member.

* * * * *